US011289194B1

(12) United States Patent
Pipher et al.

(10) Patent No.: US 11,289,194 B1
(45) Date of Patent: Mar. 29, 2022

(54) MODULAR LOCATION ENGINE FOR TRACKING THE LOCATIONS OF ASSETS IN A CLINICAL ENVIRONMENT

(71) Applicant: Hill-Rom Services, Inc., Batesville, IN (US)

(72) Inventors: Britten J. Pipher, Fuquay-Varina, NC (US); Eugene G. Urrutia, Apex, NC (US); Stephen R. Embree, Chapel Hill, NC (US); Matthew D. Morgan, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 17/003,930

(22) Filed: Aug. 26, 2020

Related U.S. Application Data

(60) Provisional application No. 62/892,417, filed on Aug. 27, 2019.

(51) Int. Cl.
| | |
|---|---|
| *G16H 40/67* | (2018.01) |
| *H04W 4/02* | (2018.01) |
| *H04W 4/029* | (2018.01) |
| *G16H 40/20* | (2018.01) |

(52) U.S. Cl.
CPC ............ *G16H 40/67* (2018.01); *G16H 40/20* (2018.01); *H04W 4/023* (2013.01); *H04W 4/029* (2018.02)

(58) Field of Classification Search
CPC ....... G16H 40/67; G16H 40/20; H04W 4/029; H04W 4/023
See application file for complete search history.

(56) References Cited

U.S. PATENT DOCUMENTS

| | | | |
|---|---|---|---|
| 6,580,393 B2 | 6/2003 | Holt | |
| 7,899,006 B2 | 3/2011 | Boyd | |
| 8,031,120 B2 | 10/2011 | Smith et al. | |
| 8,838,481 B2 * | 9/2014 | Moshfeghi | ............ G01S 5/021 |
| | | | 705/16 |
| 9,513,370 B2 | 12/2016 | Cristache | |
| 9,571,143 B2 | 2/2017 | Richley | |
| 9,641,964 B2 | 5/2017 | Kulkarni et al. | |
| 9,860,688 B2 | 1/2018 | Kulkarni et al. | |
| 9,866,507 B2 | 1/2018 | Frenkel et al. | |

(Continued)

OTHER PUBLICATIONS

"Asset Tracking System in Real Time," Litum, retrieved from <<https://litum.com/our-solutions/real-time-asset-tracking>> on Aug. 26, 2020, available as early as Apr. 11, 2019, 5 pages.

(Continued)

*Primary Examiner* — Mohamed Barakat
(74) *Attorney, Agent, or Firm* — Lee & Hayes, P.C.

(57) ABSTRACT

A location system can be used to identify locations of assets in a clinical environment. An example location system receives, from a primary receiver, timing data indicating times at which multiple receivers including the primary receiver received a wireless signal from a tag. The multiple receivers may be located in the clinical environment. The example location system further identifies that the timing data includes a flag indicating that a user of the tag has requested assistance, identifies an identifier of the tag based on the timing data; and transmits, to a reporting system, a first message indicating an identifier of the tag and that the user of the tag has requested assistance.

20 Claims, 9 Drawing Sheets

(56) References Cited

U.S. PATENT DOCUMENTS

| | | | | |
|---|---|---|---|---|
| 2003/0039248 | A1* | 2/2003 | Weaver | H04L 12/6418 370/392 |
| 2008/0094228 | A1* | 4/2008 | Welch | G16H 10/65 340/573.1 |
| 2011/0211563 | A1* | 9/2011 | Herrala | H04W 4/029 370/338 |
| 2013/0254304 | A1* | 9/2013 | Van Nest | G06Q 20/20 709/206 |
| 2013/0285794 | A1* | 10/2013 | Hansen | H04L 12/1813 340/8.1 |
| 2014/0361875 | A1* | 12/2014 | O'Hagan | G09B 19/0038 340/8.1 |
| 2016/0117915 | A1* | 4/2016 | Llewellyn, Jr. | G08B 25/12 340/573.1 |

OTHER PUBLICATIONS

"Cisco Kinetic Edge & Fog Processing Module," Cisco, retrieved from <<https://www.cisco.com/c/dam/en/us/solutions/collateral/internet-of-things/cisco-kinetic-efm-whitepaper.pdf>> on Apr. 11, 2019, published Mar. 31, 2018, 26 pages.

Costin, A. et al., "Fusing Passive RFID and BIM for Increased Accuracy in Indoor Localization," Visualization in Engineering, 3:17, Dec. 2015, 20 pages.

D'Souza, M., et al., "Evaluation of Realtime People Tracking for Indoor Environments Using Ubiquitous Motion Sensors and Limited Wireless Network Infrastructure," Pervasive and Mobile Computing, vol. 9, Issue 4, Aug. 2013, Abstract, 2 pages.

D'Souza, M. et al., "Indoor Position Tracking Using Received Signal Strength-based Fingerprint Context Aware Partitioning," IET Radar, Sonar and Navigation, vol. 10, Issue 8, Oct. 2016, 18 pages.

"Function Description—Location in Ascom VoWiFi System," TD92607GB, retrieved from <<http://www.ascomwireless.com/pdf/guide/vowifi/location_vowifi_fd_92607gb.pdf>> on Apr. 15, 2019, published Dec. 13, 2010, 11 pages.

Kwan, Dennis, "Bluetooth Mesh Profile Applied to RTLS," Bluetooth Blog, retrieved from <<https://blog.bluetooth.com/bluetooth-mesh-profile-applied-to-rtls>> on Apr. 11, 2019, published Oct. 30, 2017, 5 pages.

Miekk-oja, V., "Static Beacons Based Indoor Positioning Method for Improving Room-level Accuracy," Aalto University School of Electrical Engineering, Apr. 28, 2015, 87 pages.

Najib, et al., "A Software Development Model for Localization Systems," retrieved from <<https://www.researchgate.net/publication/228343991_A_Software_Development_Model_for_Localization_Systems>> on Apr. 15, 2019, published May 2009, 6 pages.

"High-Precision RTLS," Redpoint Positioning, retrieved from <<https://www.redpointpositioning.com/wp-content/uploads/2015/06/RedpointSolutionsBrochure.pdf>> on Apr. 11, 2019, published Jun. 27, 2015, 4 pages.

Schmitt, S., et al., "The Effects of Human Body Shadowing in RF-based Indoor Localization," 2014 International Conference on Indoor Positioning and Indoor Navigation, Oct. 2014, 8 pages.

Trogh J., et al., "Enhanced Indoor Location Tracking Through Body Shadowing Compensation," Department of Information Technology, iMinds—Ghent University, Dec. 2015, 9 pages.

* cited by examiner

MODULAR LOCATION ENGINE FOR TRACKING THE LOCATIONS OF ASSETS IN A CLINICAL ENVIRONMENT

CROSS-REFERENCE TO RELATED APPLICATIONS

This application claims the benefit of U.S. Provisional Application No. 62/892,417, filed on Aug. 27, 2019, which is incorporated by reference herein in its entirety.

TECHNICAL FIELD

This application relates generally to a Real Time Locating System (RTLS) configured to track the locations of assets in a clinical environment and to report whether a user has requested assistance in the clinical environment. This application further relates to an RTLS configured to store partially processed data for further analysis.

BACKGROUND

Hospitals, and other types of healthcare environments, track a variety of different assets, and determining/monitoring the locations of such assets can be important when administering care to patients. For instance, the positions of medical devices, hospital beds, and other clinically relevant objects may be relevant to providing and maintaining a high level of care in these environments. In various examples, the positions of patients may be significant for managing their care. In various cases, the positions of care providers (e.g., nurses, physicians, and the like) may also be important for efficiently delivering care in the clinical environment. Tracking the positions of these and other clinically relevant assets in real time can enable centralized systems (e.g., nurse call systems) within the clinical environment to efficiently deploy resources to care for the patients in the clinical environment.

An RTLS can be used to track the locations of objects and people in various settings. In the RTLS, a tag may emit a wireless signal that can be received by multiple receivers. Based on the times-of-flights (or angles-of-arrival) of the wireless signal being received by the multiple receivers, and the positions of the receivers, a tag's location can be derived within an environment.

However, broad adoption of RTLS in healthcare settings to track objects, patients, and care providers is not without challenges. There is a need for more accurate RTLS technologies adapted for various healthcare environments. In addition, due to significant variances between various healthcare environments, there is a need for a flexible RTLS platform that can be adapted for various clinical settings.

SUMMARY

Various implementations of the present disclosure relate to a modular location engine in a location system, such as an RTLS-based system, that can identify the locations of tags in a clinical environment. The location engine can be arranged into multiple network nodes that individually contribute to estimating the location of the tags in the clinical environment. The network nodes may be arranged in series, in parallel, or both, such that an output of one network node may be the input of another network node. In some implementations, the location engine can be implemented as a process (e.g., program) executing in a single operating system.

In some cases, the tags can be outfitted with triggers by which care providers or patients can request additional assistance from care providers in the clinical environment. Due to the modular arrangement of nodes in various implementations, the location engine can efficiently identify the locations of individuals in need of assistance. In some cases, the location engine may prioritize individuals according to the urgencies of the assistance they may require. Furthermore, various reporting systems can be utilized to efficiently deploy care providers that can provide the assistance to the individuals.

In some cases, individual network nodes may be configured to store their inputs or outputs in a local database. The storage of the inputs and/or outputs can be used to assist with debugging problems in the location engine, or the RTLS itself. For instance, if a network node among multiple network nodes is malfunctioning within the location engine, it may be impossible to identify which network node is malfunctioning by only evaluating the estimated locations produced by the location engine as a whole. An individual malfunctioning node can be specifically identified within the location engine by evaluating the inputs and/or outputs of individual nodes within the location engine.

The stored inputs and/or outputs can be used as a development tool to monitor changes to individual network nodes. For example, if a single network node is modified by a developer, the developer can compare the stored inputs and outputs of the network node before and after modification to identify whether the modification is working as expected. The stored inputs and/or outputs can be used to validate changes to individual network nodes.

In addition, the stored inputs and/or outputs can be used as an Information Technology (IT) assistance tool. If an RTLS system appears to be malfunctioning, the stored inputs and/or outputs can be used by an IT professional to identify whether the location engine, or some other part of the RTLS system, needs to be updated. In addition, the stored inputs and/or outputs can be used to identify and/or quantify improvements in location estimation accuracy and latency provided by updates to the location system.

DESCRIPTION OF THE FIGURES

The following figures, which form a part of this disclosure, are illustrative of described technology and are not meant to limit the scope of the claims in any manner.

DETAILED DESCRIPTION

Figure 1:
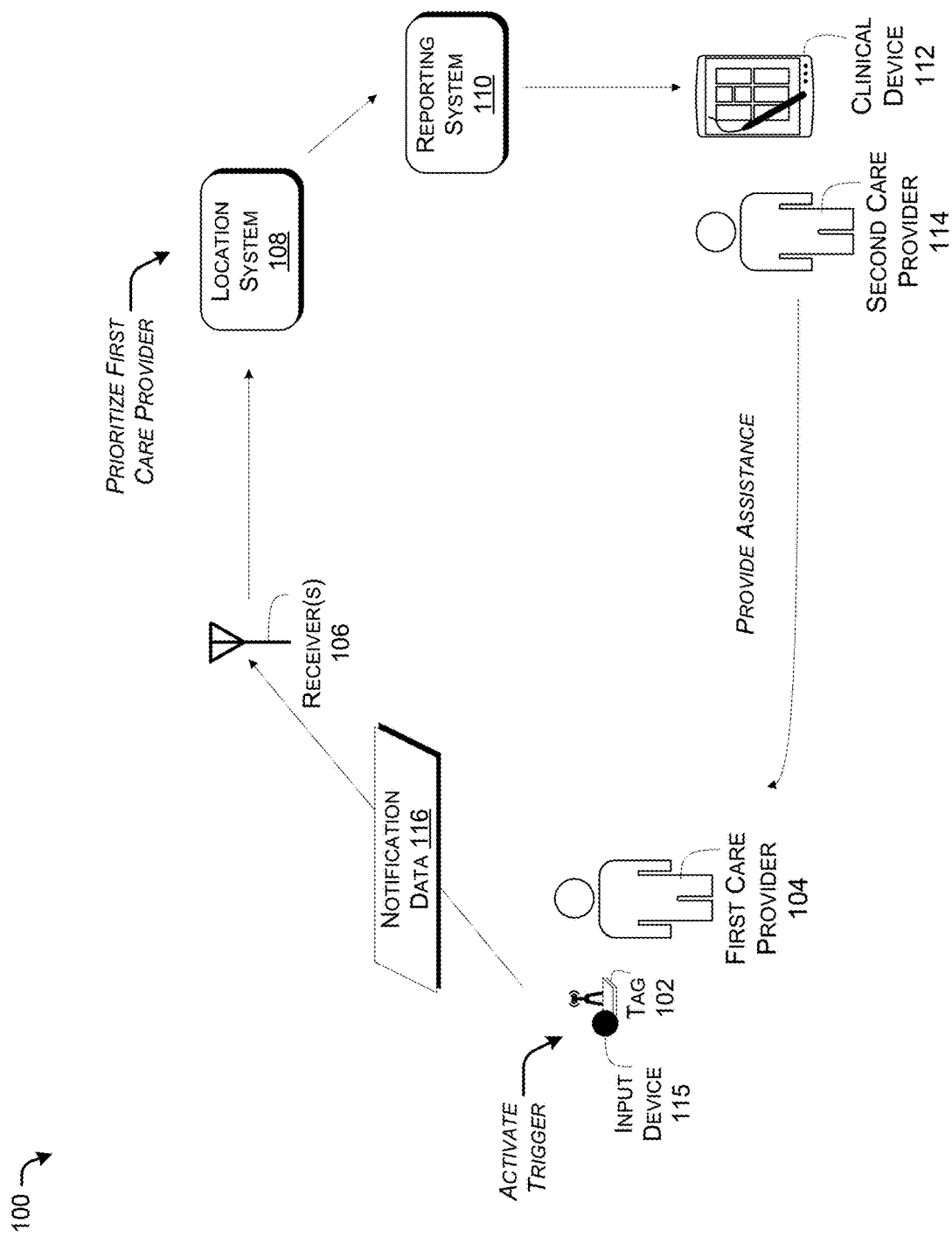
FIG. 1 illustrates an example environment for tracking tag notifications in a clinical setting.

Various implementations of the present disclosure will be described in detail with reference to the drawings, wherein like reference numerals present like parts and assemblies throughout the several views. Additionally, any samples set forth in this specification are not intended to be limiting and merely set forth some of the many possible implementations.

FIG. 1 illustrates an example environment 100 for tracking tag notifications in a clinical setting. The environment 100 may be part of or may include an RTLS, in some cases. As illustrated in FIG. 1, a tag 102 may be associated with a first care provider 104. In various implementations, the tag 102 may transmit wireless signals to one or more receivers 106 in a clinical environment, such as a hospital. As used herein, the term "tag" can refer to a physical device capable of storing information, transmitting information to a remote device, and/or receiving information from a remote device. A tag may be attached to a physical object (e.g., a medical device, a hospital bed, or the like). In various implementations, a tag can be passive, such that it collects energy from outside sources (e.g., radio waves) to power storage, data transmission, processing, or the like. In some implementations, a tag can be active, such that it may include a power source that can be used to power storage, data transmission, processing, or the like. Some examples of tags include Radio-Frequency Identification (RFID) tags, which can use electromagnetic signals to communicate with external devices. However, some tags can use non-radio-frequency electromagnetic signals, acoustic signals, or the like to communicate with external devices.

The receiver(s) 106 may receive the wireless signals from the tag 102. For example, the receiver(s) 106 may measure times at which the wireless signals are received at the receiver(s) 106, angles at which the wireless signals are received at the receiver(s) 106, or the like. The receiver(s) 106 may transmit indications of the wireless signals (e.g., timing and/or angle measurements) to a location system 108, which may identify the position of the tag 102 in the clinical environment based on the transmissions. The location system 108 may provide the position of the tag 102 to a reporting system 110. The reporting system 110 may communicate one or more alerts to a clinical device 112 based on the location of the tag 102. The alert(s) can be output by the clinical device 112 to a second care provider 114. The second care provider 114 may provide assistance to the first care provider 104 based on the alert(s). Various implementations of this basic environment will be described further below with reference to FIGS. 5 to 9.

In various implementations, the first care provider 104 may identify that he or she requires assistance. In some cases, the first care provider 104 can request assistance using the tag 102 itself. The first care provider 104 can request assistance by activating a trigger on the tag. For instance, the tag 102 may include an input device 115 (e.g., a button or other input mechanism) that can be used to request assistance from the second care provider 114. In response to an input being received at the input device 115, the trigger may be activated, and the tag 102 may generate the wireless signals to include notification data 116 indicating that the first care provider 104 has requested assistance. For instance, the notification data 116 can be included in a payload of a data packet transmitted in the wireless signals. In some cases, the notification data 116 can include a flag, which may be a specific code in the wireless signal that indicates the first care provider 104 has requested assistance. In some cases, the notification data 116 may include and/or be incorporated into a blink signal that can be used by the location system 108 to identify the location of the tag 102. In some examples, a blink may be transmitted by the tag 102 separately from the notification data 116.

The receiver(s) 106 may forward the notification data 116 with the measurements to the location system 108. Based on the notification data 116, the location system 108 may identify that the tag 102 has been triggered. The location system 108 may notify the reporting system 110 that the tag 102 has been triggered, along with the location of the tag 102.

In some cases, the reporting system 110 may cause the clinical device 112 to output, to the second care provider 114, an alert that the first care provider 104 requires assistance. In some cases, the alert also indicates the location of the first care provider 104. Accordingly, the second care provider 114 may be directed to provide assistance to the first care provider 104. In some examples, the reporting system 110 may transmit one or more signals that cause the clinical device 112 to output an indication of the location of the tag 102. In some cases, the one or more signals may cause the clinical device 112 to output an instruction to provide assistance to the first care provider 104. In some cases, the reporting system 110 may determine that the tag 102 is associated with the first care provider 104 and may output, to the clinical device 112, one or more signals causing the clinical device 112 to output an identifier (e.g., a name, an employee identifier, or the like) of the first care provider 104.

Various implementations of the present disclosure can also be used in other examples. For instance, instead of a care provider 104 activating the trigger, in some cases, a patient in need of assistance may activate the trigger. Thus, in various examples, various implementations described herein may facilitate calls for assistance within the environment 100.

Figure 2:
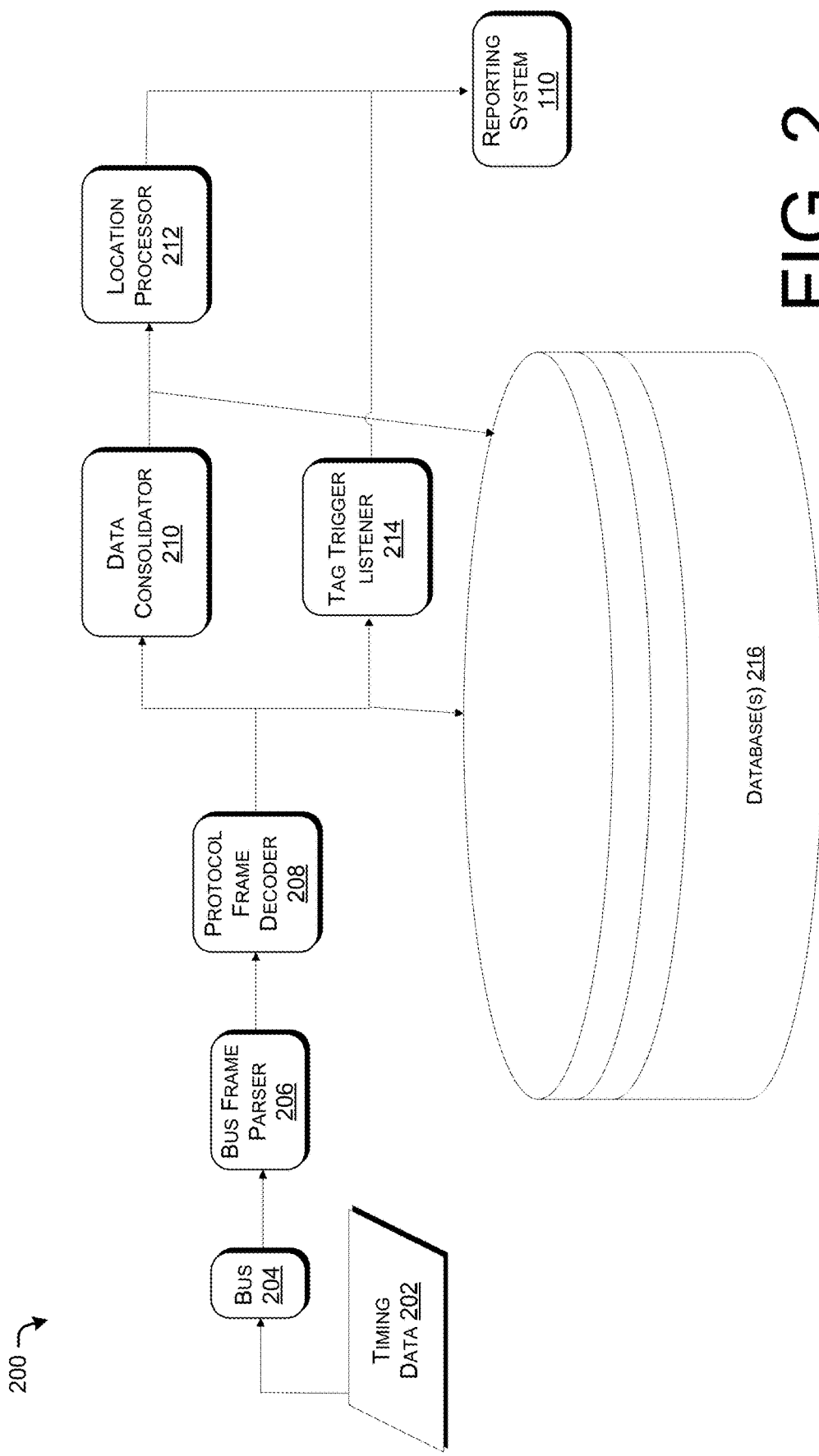
FIG. 2 illustrates an example of a modular location system.

FIG. 2 illustrates an example of a modular location system 200. In particular, the modular location system 200 includes functionality that enables the prioritization of identifying and locating tags with active triggers in a clinical environment. In addition, the modular location system 200 is an effective platform for debugging problems associated with the location system. Various components of the modular location system 200 can be implemented in hardware, in software, or a combination thereof.

Timing data 202 may be input into a bus 204. In some cases, the timing data 202 may include notification data. As used herein, the term "bus," and its equivalents, can refer to a system that transfers data between different components within one or more computing systems. A bus can be implemented in hardware, software, or a combination thereof. The bus 204 may receive the timing data 202 from various receivers in the clinical environment. The bus 204 may aggregate the timing data into a single data stream. However, the timing data in the data stream generated by the bus 204 may be in a format that is difficult to analyze directly. For example, the bus 204 may aggregate the timing data into a particular communication protocol that combines data from multiple receivers and associated with multiple tags into a data stream, such that it may be difficult to extract data from a single receiver and/or associated with a single tag from the data stream. Accordingly, it may be further processed by a bus frame parser 206 and/or a protocol frame decoder 208.

The bus frame parser 206 may parse raw data from the bus 204 into individual data frames for further processing. For instance, the bus frame parser 206 may receive a stream of raw serial data from the bus 204. The stream of raw serial data may include headers, encoded messages, and checksums representing data from various receivers. The bus frame parser 206 may extract the encoded messages and output the encoded messages.

The output from the bus frame parser 206 may be input into the protocol frame decoder 208. In various implementations, the protocol frame decoder 208 may be decode the encoded messages output from the bus frame parser 206. In some cases, the decoded messages may be output as software objects. The output from the protocol frame decoder 208 may include consolidated data representing timestamps associated with times that receivers received wireless signals from various tags in the clinical environment, identifiers of the tags, as well as notification data, if applicable. According to various examples, an identifier of a tag can be a unique string, number, and/or code associated with the tag. In an environment including multiple tags, each tag may be associated with a unique identifier. In some cases, the output from the protocol frame decoder 208 can include a stream of data that is not sorted according to individual tags or individual wireless signals transmitted by the tags.

In various implementations, at least one of the bus 204, the bus frame parser 206, or the protocol frame decoder 208 may be substituted for any suitable timing data gateway. The timing data gateway may be any gateway that can transfer data between sensors (e.g., RTLS receivers) and a system configured to identify tag locations based on measurements or other data from the sensors (e.g., a location engine). In some cases, the timing data gateway may include at least one of a Bluetooth interface, a wireless mesh network, a wireless access point, a WiFi network, or the like.

The output of the protocol frame decoder 208 may be separately input into a data consolidator 210 and a tag trigger listener 214. The consolidator 210 may group together data in the output from the protocol frame decoder 208 into individual messages sorted by individual wireless signals transmitted by individual tags. These messages can be individual data packets, in some cases.

The output from the data consolidator 210 may be input into the location processor 212. The location processor 212 can identify the locations of the tags based on the messages provided by the data consolidator 210. In some cases, the location processor 212 may perform time synchronization on the messages, to ensure that different measurements from different receivers in the RTLS system are compared according to the same time reference. Various strategies for identifying the locations of tags are described below with reference to FIGS. 5 to 9.

The tag trigger listener 214 may evaluate the unconsolidated messages output by the protocol frame decoder 208 to identify whether they include flags indicating notification data. Accordingly, the tag trigger listener 214 may identify whether a tag is triggered, and whether an individual associated with the tag is in distress. In some cases, the tag trigger listener 214 may be implemented as at least one VM, at least one software instance hosted on at least one device (e.g., a server), a single software instance hosted on multiple devices, or the like.

In various implementations, the data consolidator 210 requires substantial processing of the data stream output by the protocol frame decoder 208. The data consolidator 210 therefore introduces substantial latency into the processing of the timing data 202 within the location system 200. The latency introduced by the data consolidator 210 can be problematic when the location system 200 is determining whether an individual requires immediate or emergency assistance in response to triggering a tag in the clinical environment. Accordingly, in some examples, the output from the protocol frame decoder 208 bypasses the data consolidator 210 and is input directly into the tag trigger listener 214.

When the tag trigger listener 214 identifies that a flag (e.g., a specialized 32-bit code) is present in a message output from the protocol frame decoder 208, the tag trigger listener 214 may immediately notify the reporting system 110. The tag trigger listener 214 can identify the tag that is triggered based on the message output from the protocol frame decoder 208 and provide an identifier of the tag to the reporting system 110. Accordingly, regardless of whether a location of the tag has been identified by the location processor 212, the reporting system 212 may trigger an alert associated with the tag and/or an individual that the reporting system 212 knows is associated with the tag. Because the data consolidator 210 and the location processor 212 can be bypassed in the location system 200, the alert associated with the triggered tag can be output almost immediately after the tag is triggered.

In some examples, the flag is represented as a counter. In some cases, the counter may be represented by 8 bits, 16 bits, 32 bits, or some other suitable number of bits. When the tag is triggered, the counter may increment (e.g., by one). The tag trigger listener 214 may store a previous counter value associated with the tag. The tag trigger listener 214 may compare the previous counter value to a counter value represented by the message output from the protocol frame decoder 208. If the previous counter value is different from the counter value represented by the message, the tag trigger listener 214 may determine that the tag has been triggered. Accordingly, if a first message carrying the flag (i.e., the incremented counter) is lost before or within the location system 200, the tag trigger 214 may nevertheless identify that the tag has been triggered based on a subsequent message.

The output from the location processor 212, as well as the output from the tag trigger listener, may be input into the reporting system 110. Accordingly, the reporting system 110 can efficiently identify individual tags whose triggers have been activated, as well as their locations. In some cases, the reporting system 110 can include a visualization tool that enables a device to output an image depiction of the locations of the tags within the clinical environment.

In addition, the various outputs from nodes within the modulation location system 200 can be stored in at least one database 216. For instance, the unconsolidated timestamp data output by the protocol frame decoder 208 can be saved to the database(s) 216. In some cases, the unconsolidated timestamp data can be stored as a Comma-Separated-Value (CSV) file. In addition, the consolidated messages output by the data consolidator 210 can be saved to the database(s) 216. In some cases, the outputs can be stored in the database(s) 216 via a Publication-Subscribe (Pub Sub) module in series between any of the nodes.

In various implementations, the unconsolidated timestamp data and/or the consolidated messages can be accessed in the database(s) 216 to perform a debugging operation. For instance, a developer may cause the location system to input past unconsolidated timestamp data into the data consolidator 210 and compare the output of the data consolidator 210 to past consolidated messages stored in the database to determine whether the data consolidator 210 has begun to malfunction. In some cases, an IT expert can similarly perform tests comparing the outputs of the bus 204, bus frame parser 206, protocol frame decoder 208, data consolidator 210, location processor 212, tag trigger listener 214, the timing gateway, and the like to previously observed outputs stored in the database(s) 216, even while the location system 200 is actively performing in a clinical environment. Various evaluations using the data stored in the database(s) 216 can be used to identify and/or diagnose problems associated with nodes within the location system 200. In various implementations, at least one of the bus 204, the bus frame parser 206, the protocol frame decoder 208, the data consolidator 210, the location processor 212, the tag trigger listener 214, or the timing gateway may represent nodes within the location system 200.

In addition, various evaluations can be used to identify the accuracy of locations produced by the location processor 212. For instance, ideal consolidated messages can be input into the location processor 212 and the output of the location processor 212 can be compared to known locations corresponding to the ideal consolidated messages. Accordingly, the amount of error introduced by the location processor 212 can be identified and used to improve the design of the location processor 212.

Figure 3:
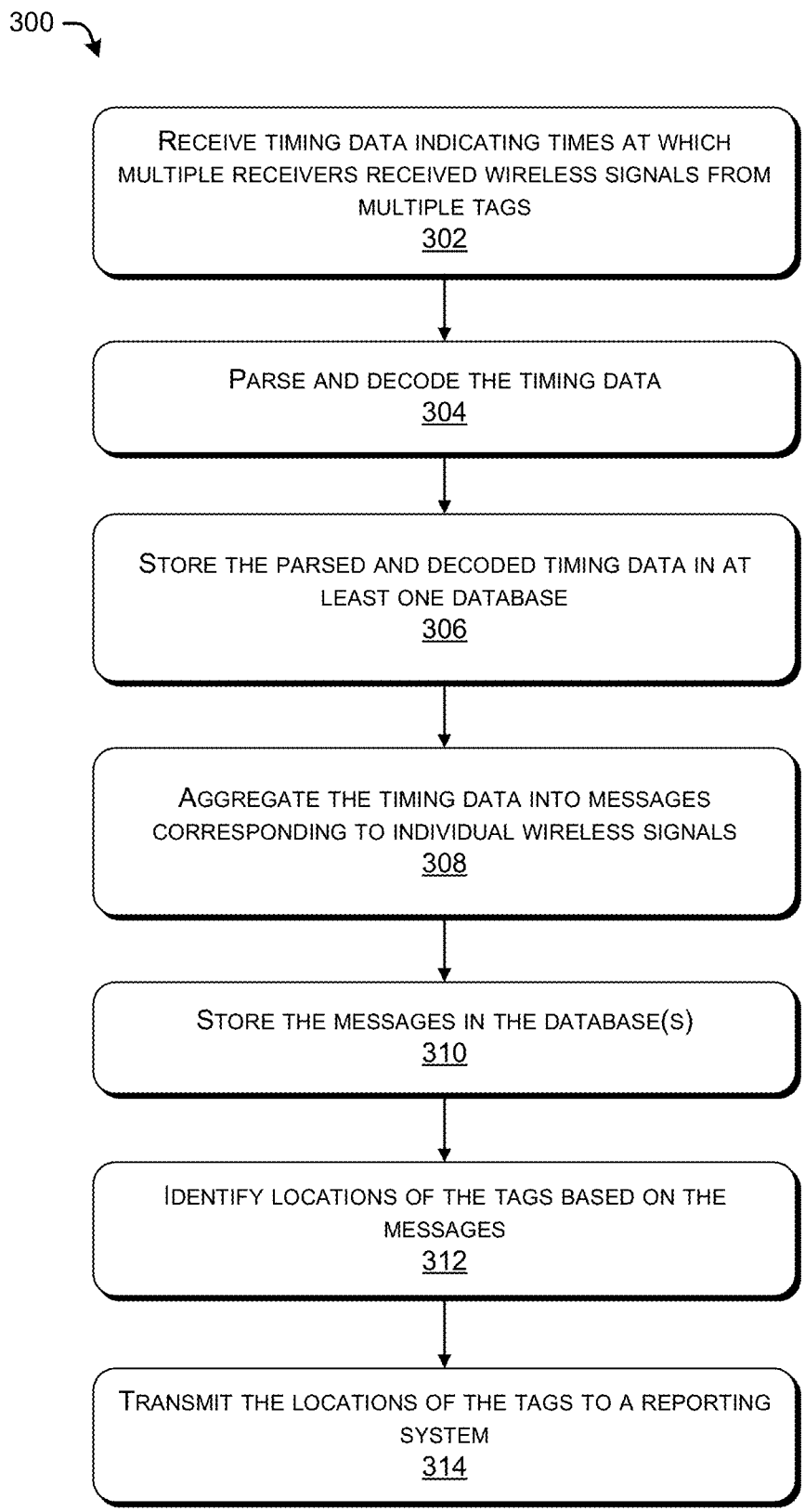
FIG. 3 illustrates an example process for identifying the locations of tags within a clinical environment.

FIG. 3 illustrates an example process 300 for identifying the locations of tags within a clinical environment. In various implementations, the example process 300 can be performed by a modular location system, such as the location system 108 described above with reference to FIG. 1 or the location system 200 described above with reference to FIG. 2. In some implementations, the process 300 can be performed by one or more processors within a system.

At 302, the processor(s) may receive timing data via one or more transceivers. The timing data may indicate times at which multiple receivers arranged in the clinical environment received wireless signals from multiple tags. In some cases, the multiple tags are collocated with assets, such as physical objects (e.g., medical devices, hospital beds, and the like) or individuals (e.g., care providers, patients, and the like). Accordingly, the locations of the tags can be used to identify the locations of the assets.

At 304, the processor(s) may parse and decode the timing data. In some implementations, the timing data may be in a format that is not conducive to aggregation and analysis. By parsing and decoding the timing data, the processor(s) may be enabled to perform further analysis on the timing data.

At 306, the processor(s) may store the parsed and decoded timing data in at least one database. By storing the parsed and decoded timing data, the system may later perform tests on various nodes throughout the location system in order to debug and/or identify problems in the individual nodes.

At 308, the processor(s) may aggregate the timing data messages corresponding to individual wireless signals emitted from individual tags. One message may indicate times that various receivers throughout the clinical environment received a single wireless signal broadcast from a single tag.

At 310, the processor(s) can store the messages in the database(s). Similar to storing the parsed and decoded timing data, the processor(s) may later perform tests on various functionality throughout the location system in order to debug and/or identify problems in individual nodes within the location system. For instance, the processor(s) may identify problems associated with an aggregation node and/or functionality that performs 308.

At 312, the processor(s) can identify the locations of the tags based on the messages. For instance, the processor(s) can triangulate the location of a tag based on the times at which various receivers throughout the clinical environment received a wireless signal broadcast from the tag. Various strategies for identifying the location of the tag are described below with reference to FIGS. 5 to 8.

At 314, the processor(s) can cause the transceiver(s) to transmit one or more messages indicating the locations of the tags to a reporting system. In some cases, the reporting system may use the locations of the tags to selectively send alerts to clinical devices within the clinical environment. For instance, if there is a patient in need of assistance and a tag associated with a care provider is determined to be within a predetermined proximity of the patient, the processor(s) may cause a clinical device associated with the care provider to output an instruction to assist the patient.

Figure 4:
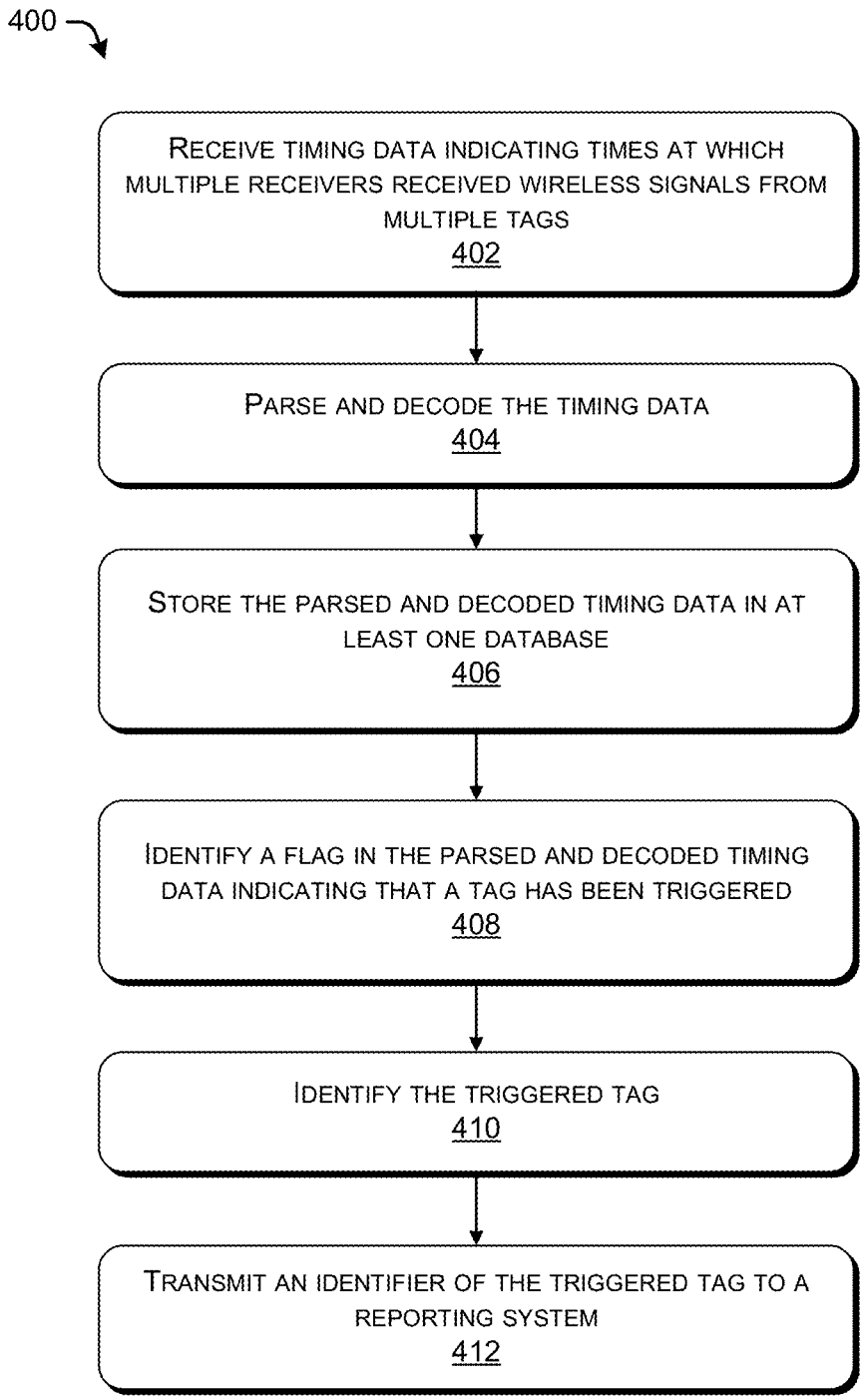
FIG. 4 illustrates an example process for identifying whether a tag has been triggered.

FIG. 4 illustrates an example process 400 for identifying whether a tag has been triggered. In various implementations, the example process 400 can be performed by a modular location system, such as the location system 108 described above with reference to FIG. 1 or the location system 200 described above with reference to FIG. 2. In some implementations, the process 300 can be performed by one or more processors within a system.

At 402, the processor(s) may receive timing data via one or more transceiver(s). The timing data may indicate times at which multiple receivers arranged in the clinical environment received wireless signals from multiple tags. In some cases, the multiple tags are collocated with assets, such as objects (e.g., medical devices, hospital beds, and the like) or individuals (e.g., care providers, patients, and the like). Accordingly, identifying the locations of the tags can be used to identify the locations of the assets. In various implementations, the timing data may further include notification data indicating that one or more of the tags has been triggered.

At 404, the processor(s) may parse and decode the timing data. In some implementations, the timing data may be in a format that is not conducive to aggregation and analysis. By parsing and decoding the timing data, the processor(s) may be enabled to perform further analysis on the timing data.

At 406, the processor(s) may store the parsed and decoded timing data in at least one database. By storing the parsed and decoded timing data, the processor(s), or some other device, may later perform tests on various nodes throughout the location system in order to debug and/or identify problems in the individual nodes. For example, the parsed and decoded timing data can be compared to expected data, to determine whether any of the individual nodes malfunctioned while generating the parsed and decoded timing data.

At 408, the processor(s) may identify a flag in the parsed and decoded timing data. The flag may indicate that a particular tag among the multiple tags has been triggered. In some cases, the flag may be a predetermined code within the timing data. Accordingly, the processor(s) may read the parsed and decoded timing data in order to identify that the flag is present in the parsed and decoded timing data.

At 410, the processor(s) may identify the triggered tag. For instance, when the processor(s) identifies the triggered tag in a message indicating at least one time at which at least one receiver received the wireless signal including the notification data, the processor(s) may further extract an identifier of the triggered tag in the message. In some cases, each tag tracked within the clinical environment may have a proprietary identification code that the tag includes in each wireless signal transmitted to the receivers (e.g., a 32-bit code). The processor(s) may extract that identification code from the message.

At 412, the processor(s) may cause the transceiver(s) to transmit the identifier to a reporting system. In some cases, the reporting system may selectively transmit an alert indicating the identifier of the tag, a user associated with the tag, a location of the tag, or the like, to at least one clinical device in the clinical environment. Accordingly, a user of the clinical device may be prompted to assist the user that triggered the tag and requested assistance.

Figure 5:
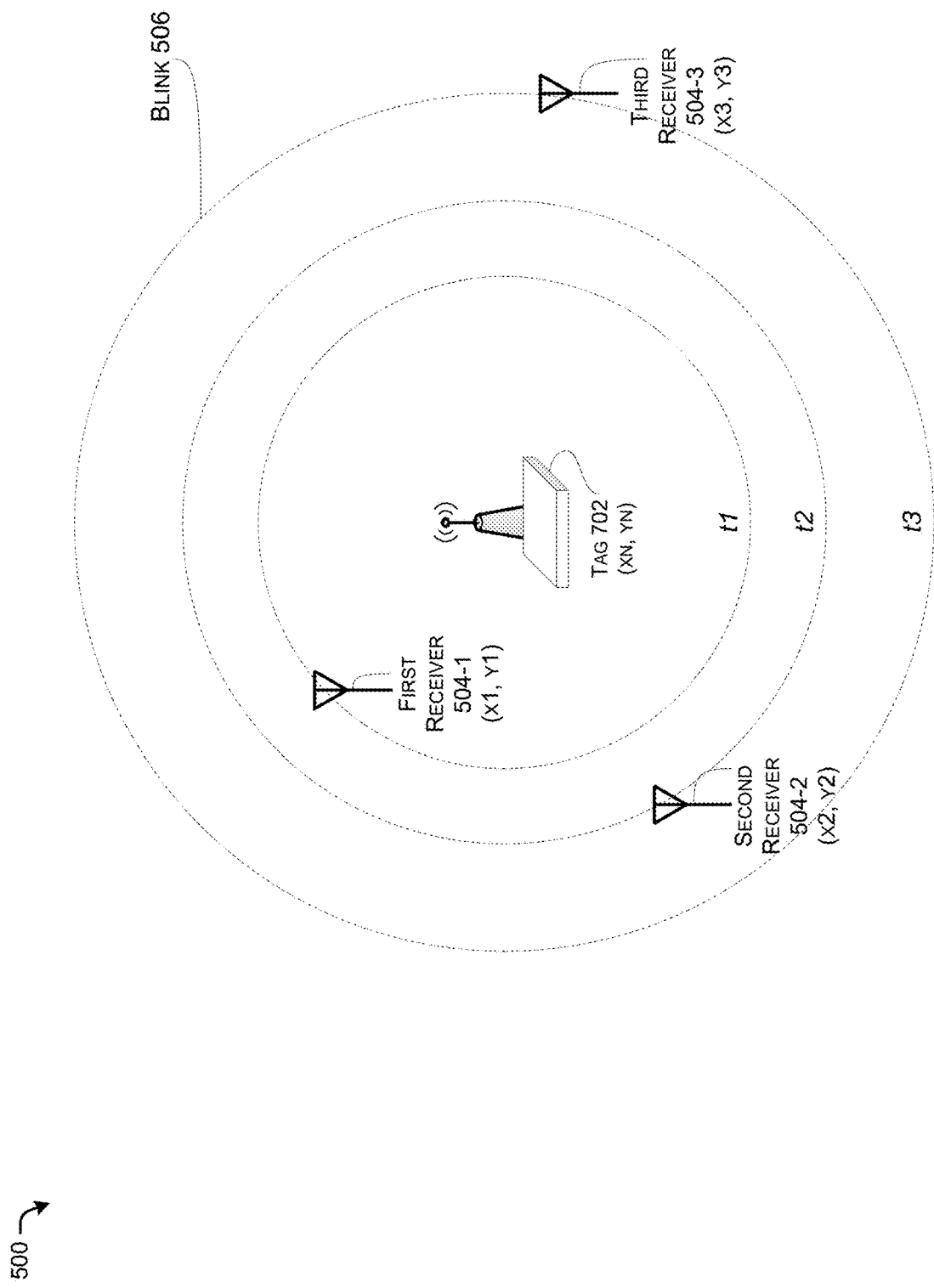
FIG. 5 illustrates an example location system environment.

FIG. 5 illustrates an example location system environment 500. As illustrated, the environment 500 includes a tag 502 and multiple receivers 504-1 to 504-3. In various implementations, the tag 502 is configured to broadcast wireless signals. In some cases, the tag 502 may broadcast the wireless signals periodically. For instance, the tag 502 may be configured to broadcast the wireless signals at a frequency of once every five minutes, once a minute, twice a minute, once every ten seconds, once a second, multiple times per second, or the like. According to some examples in which the tag 502 is carried or affixed by a moving object or person, the tag 502 may broadcast the wireless signals at a frequency of once every 10-1000 milliseconds.

In some cases, the tag 502 may broadcast the wireless signals in response to an event. For instance, the tag 502 may broadcast the wireless signals in response to receiving a request for the wireless signals from another device, or in response to some other type of event. The wireless signals can be electromagnetic signals (e.g., infrared signals, radio signals, etc.), ultrasonic signals, subsonic signals, or the like.

The receivers 504-1 to 504-3 are configured to receive the wireless signals from the tag 502, and to recognize the times at which the wireless signals are received. In some cases, the receivers 504-1 to 504-3 each include various components of the device(s) 900 described below with reference to FIG. 9. For instance, the receivers 504-1 to 504-3 may have receivers configured to receive the wireless signals from the tag 502, an analog-to-digital converter configured to generate digital data based on the wireless signals, a clock configured to identify a reception time (e.g., a time-of-arrival) of the wireless signal. One or more processors may be configured to identify the identity of the tag 502 from the wireless signals, identify the reception time by referencing the clock, and generate timing data and/or a timing report indicating an identifier of the tag 502 and the reception time. According to various examples, the identifier of the tag 502 can be a unique string, number, and/or code associated with the tag 502. In an environment including multiple tags, each tag may be associated with a unique identifier. The receivers 504-1 to 504-3 may be referred to as "anchors" in some cases.

In various implementations, the receivers 504-1 to 504-3 are located at known positions. In some implementations, the receivers 504-1 to 504-3 may be mounted at fixed positions on walls, ceilings, or fixtures within a hospital building. The receivers 504-1 to 504-3 may be located at different positions. As illustrated in FIG. 5, a first receiver 504-1 may be located at position ($x_1$, $y_1$), a second receiver 504-2 may be located at position ($x_2$, $y_2$), and a third receiver 504-3 may be located at a position ($x_3$, $y_3$). Although the environment 500 illustrated in FIG. 5 is depicted two dimensions, in some cases, the environment 500 can be defined in three dimensions.

In some cases, the receivers 504-1 to 504-3 may be further configured to communicate with each other over a wired (e.g., ethernet, fiber-optic, etc.) and/or wireless (e.g., Wi-Fi, Bluetooth, etc.) Local Area Network (LAN).

In some implementations, a single wireless signal broadcast by the tag 502 may be referred to as a "blink." As depicted in FIG. 1, an example blink 506 is transmitted from the tag 502 at time=$t_0$. The blink 506 is received at the first receiver 504-1 at time=$t_1$, at the second receiver 504-1 at time=$t_2$, and at the third receiver 504-3 at time=$t_3$.

The position of the tag 502 may be derived based on the positions of the receivers 504-1 to 504-3 and the times at which the receivers 504-1 to 504-3 receive the blink 506. In various example implementations, the distances between the tag 502 and the receivers 504-1 to 504-3 may be calculated.

In some cases, the blink 506 indicates to. At least one of the receivers 504-1 to 504-3 may be able to derive to from the blink 506. Accordingly, a time-of-flight of the blink 506 between the tag 502 and each one of the receivers 504-1 to 504-3 can be derived according to the following Formula 1:

$$\Delta t = t_n - t_0 \qquad \text{Formula 1}$$

wherein $\Delta t$ is the time-of-flight of the blink 506, $t_n$ is the time at which a receiver receives the blink 506 (e.g., $t_1$ for the first receiver 504-1, $t_2$ for the second receiver 504-2, and $t_3$ for the third receiver 504-3), and to is the time at which the tag 502 transmits the blink 506.

Based on the times-of-flight of the blink 506 between the tag 502 and the receivers 504-1 to 504-3, distances between the tag 502 and the receivers 504-1 to 504-3 can be derived based on the following Formula 2:

$$d = \Delta t * v \qquad \text{Formula 2}$$

wherein d is the distance between the tag 702 and a particular receiver, $\Delta t$ is the time-of-flight of the blink 506 between the tag 502 and the particular receiver, and v is the velocity of the blink 506. If the blink 506 is an electromagnetic signal, the velocity of the blink 506 can be estimated as the speed of light. If the blink 506 is an ultrasonic or subsonic signal, the velocity of the blink 506 can be estimated as the speed of sound (e.g., through air).

Finally, the position of the tag 502 can be calculated based on the distances between the tag 502 and the receivers 504-1 to 504-3, as well as the known positions of the receivers 504-1 to 504-3. If the position of the tag 502 is defined as ($x_n$, $y_n$), the following Formulas 3 can be used to derive the position of the tag 502:

$$d_1^2 = (x_1 - x_n)^2 + (y_1 - y_n)^2$$

$$d_2^2 = (x_2 - x_n)^2 + (y_2 - y_n)^2$$

$$d_3^2 = (x_3 - x_n)^2 + (y_3 - y_n)^2 \qquad \text{Formulas 3}$$

wherein $d_1$ is the distance between the first receiver 504-1 and the tag 502, $d_2$ is the distance between the second receiver 504-2 and the tag 502, $d_3$ is the distance between the third receiver 504-3 and the tag 502, $x_1$ is the position of the first receiver 504-1 on the x axis, $y_1$ is the position of the first receiver 504-1 on they axis, $x_2$ is the position of the second receiver 504-2 on the x axis, $y_2$ is the position of the second receiver 504-2 on they axis, $x_3$ is the position of the third receiver 504-3 on the x axis, and $y_3$ is the position of the third receiver 504-3 on they axis.

In some implementations, to may be unknown. In these cases, the position of the tag 502 can be derived by solving for $x_n$ and $y_n$ in the following Formulas 4:

$$(v(t_1 - t_0))^2 = (x_1 - x_n)^2 + (y_1 - y_n)^2$$

$$(v(t_2 - t_0))^2 = (x_2 - x_n)^2 + (y_2 - y_n)^2$$

$$(v(t_3 - t_0))^2 = (x_3 - x_n)^2 + (y_3 - y_n)^2 \qquad \text{Formulas 4}$$

wherein $t_1$, is the time at which the first receiver 504-1 receives the blink 506, $t_2$ is the time at which the second receiver 504-2 receives the blink 506, $t_3$ is the time at which the third receiver 504-3 receives the blink 506, to is the time at which the tag 502 transmits the blink 506, $x_1$ is the position of the first receiver 504-1 on the x axis, $y_1$ is the position of the first receiver 504-1 on the y axis, $x_2$ is the position of the second receiver 504-2 on the x axis, $y_2$ is the position of the second receiver 504-2 on the y axis, $x_3$ is the position of the third receiver 504-3 on the x axis, and $y_3$ is the position of the third receiver 504-3 on the y axis. Using Formulas 4 above, the to term can be eliminated and the $x_n$ and $y_n$ terms can be derived.

In some implementations, one of the receivers 504-1 to 504-3 receives timing information from the other receivers. For instance, the first receiver 504-1 may receive a timing report indicating $t_2$ from the second receiver 504-2 and may receive a timing report indicating $t_3$ from the third receiver 504-3. In some cases, the receiver with the timing information calculates the position of the tag 502. In various examples, the receiver with the timing information forwards the timing information to a location system, which can calculate the location of the tag 502 using the timing information.

According to some implementations, individual receivers calculate timing differentials representing the differences between the reception times of different receivers. For instance, upon receiving the blink 506 at $t_1$, the first receiver 504-1 may transmit a synchronization signal to the second receiver 504-2 and the third receiver 504-3. In some cases, the synchronization signal may indicate $t_1$. In some examples in which the synchronization signal is transmitted between the receivers over a high speed (e.g., wired) network, the time at which the synchronization signal is received may be estimated as $t_1$. The second receiver 504-2 may calculate the differential $t_2-t_1$, and the third receiver 504-3 may calculate the differential $t_3-t_1$ based on the synchronization signal. The second and third receivers 504-2 and 504-3 may transmit the calculated differentials back to the third receiver 504-1. In some implementations, at least one (e.g., computer) system connected to the receivers calculates the timing differentials.

Figure 6:
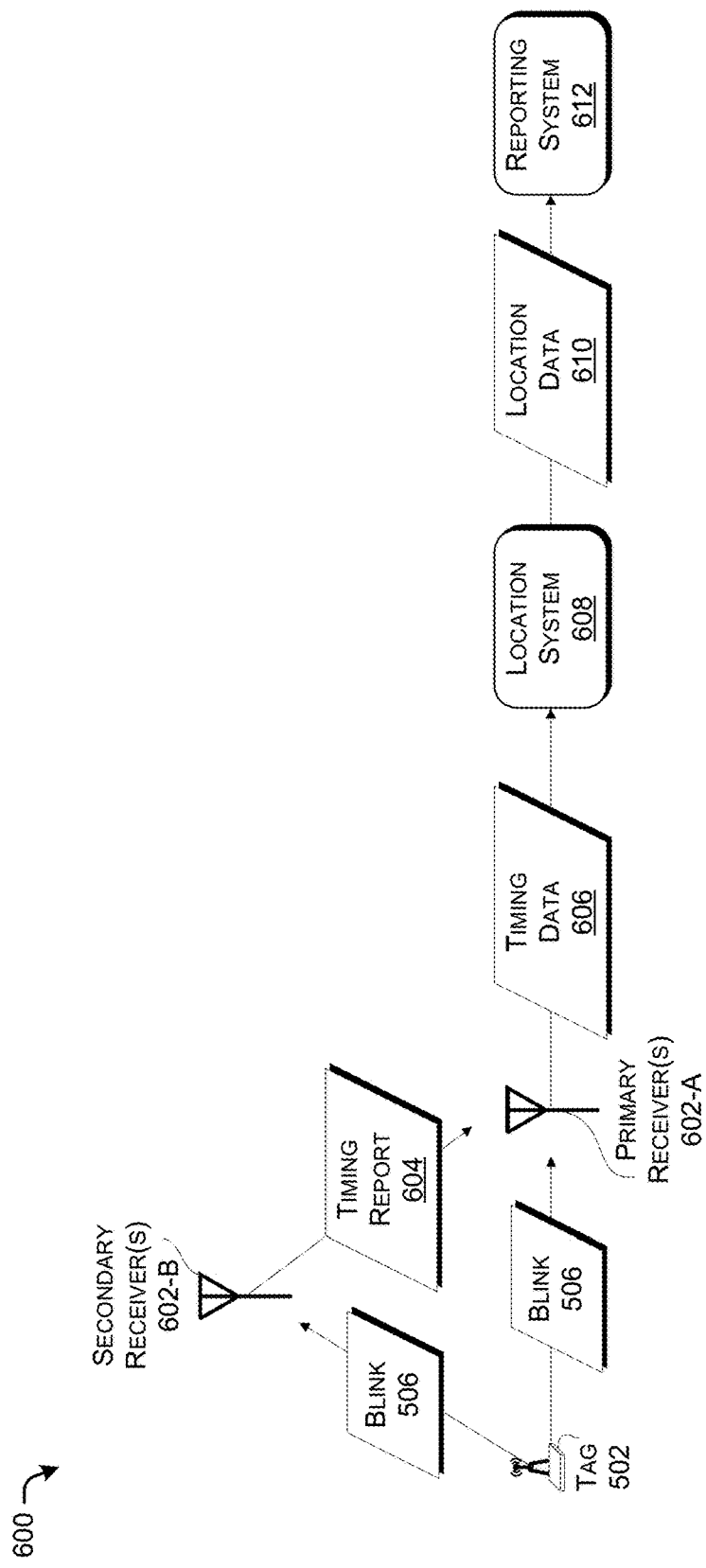
FIG. 6 illustrates an example environment for locating tags in a clinical environment.

FIG. 6 illustrates an example environment 600 for locating tags in a clinical environment. As illustrated, the environment 600 includes the tag 502 transmitting the blink 506, described above with reference to FIG. 5.

As illustrated in FIG. 6, the tag 502 transmits the blink 506 to multiple receivers 602-A and 602-B. In some implementations, the multiple receivers 602-A and 602-B can include the receivers 504-1 to 504-3 described above with reference to FIG. 5. The multiple receivers 602-A and 602-B include primary receiver(s) 602-A and secondary receiver(s) 602-B. The primary receiver(s) 602-A may be connected to the secondary receiver(s) 602-B over a wired and/or wireless Local Area Network (LAN). The secondary receiver(s) 602-B may be configured to identify time(s) when the blink 506 is received by the secondary receiver(s) 602-B and may inform the primary receiver(s) 602-A of the time(s) in a timing report 604. The timing report 604 may be transmitted over the LAN. The primary receiver(s) 602-A may be configured to identify time(s) when the blink 506 is received by the primary receiver(s) 602-A, identify time(s) when the blink 506 is received by the secondary receiver(s) 602-B based on the timing report 604, and may aggregate the times in timing data 606. The primary receiver(s) 602-A may transmit the timing data 606 to a location system 608. In some cases, the timing data 606 may indicate identifiers of the primary receiver(s) 602-A and the secondary receiver(s) 602-B along with the receipt times of the blink 506. In some examples, the timing data 606 may indicate the locations of the primary receiver(s) 602-A and the secondary receiver(s) 602-B along with the receipt times of the blink 506.

The location system 608 may be configured to identify the location of the tag 502 based on the timing data 606. In various implementations, the location system 608 can be a computer system including at least one processor configured to perform operations stored in memory. In some cases, the location system 608 may be able to identify the locations of the primary receiver(s) 602-A and the secondary receiver(s) 602-B by cross-referencing identifiers of the primary receiver(s) 602-A and the secondary receiver(s) 602-B in a database. The identifiers of the primary receiver(s) 602-A and the secondary receiver(s) 602-B may be included in the timing data 606. In some cases, the locations of the primary receiver(s) 602-A and the secondary receiver(s) 602-B may be indicated in the timing data 606 itself.

In various implementations, the location system 608 may be configured to identify the locations of multiple tags including the tag 502. To distinguish the timing data 606 associated with the tag 502 from other timing data associated with other tags, the primary receiver(s) 602-A may generate the timing data 606 indicate the identifier of the tag 502.

Once the location system 608 identifies the location of the tag 502, the location system 608 may indicate the location in location data 610. In some cases, the location data 610 may also indicate the identifier of the tag 502. The location system 608 may transmit the location data 610 to a reporting system 612. The reporting system 612 may output the location of the tag 502 and/or take various other actions based on the location of the tag 502. For instance, if the tag 502 is associated with a care provider and the reporting system 612 determines that the tag 502 is located within the vicinity of a patient in need of immediate care, the reporting system 612 may selectively notify the care provider of the patient's need and request that the care provider attend to the patient.

In various implementations, at least one of the location system 608 and the reporting system 612 may be located outside of an internal network within the clinical environment. For example, the location system 608 and/or the reporting system 612 can be implemented on one or more servers in a distributed (e.g., cloud) computing environment. At least one firewall may be disposed between the primary receiver(s) 602-A and the location system 608, within the location system 608, between the location system 608 and the reporting system 612, or within the reporting system 612. Accordingly, a security policy within the clinical environment can be enforced.

Figure 7:
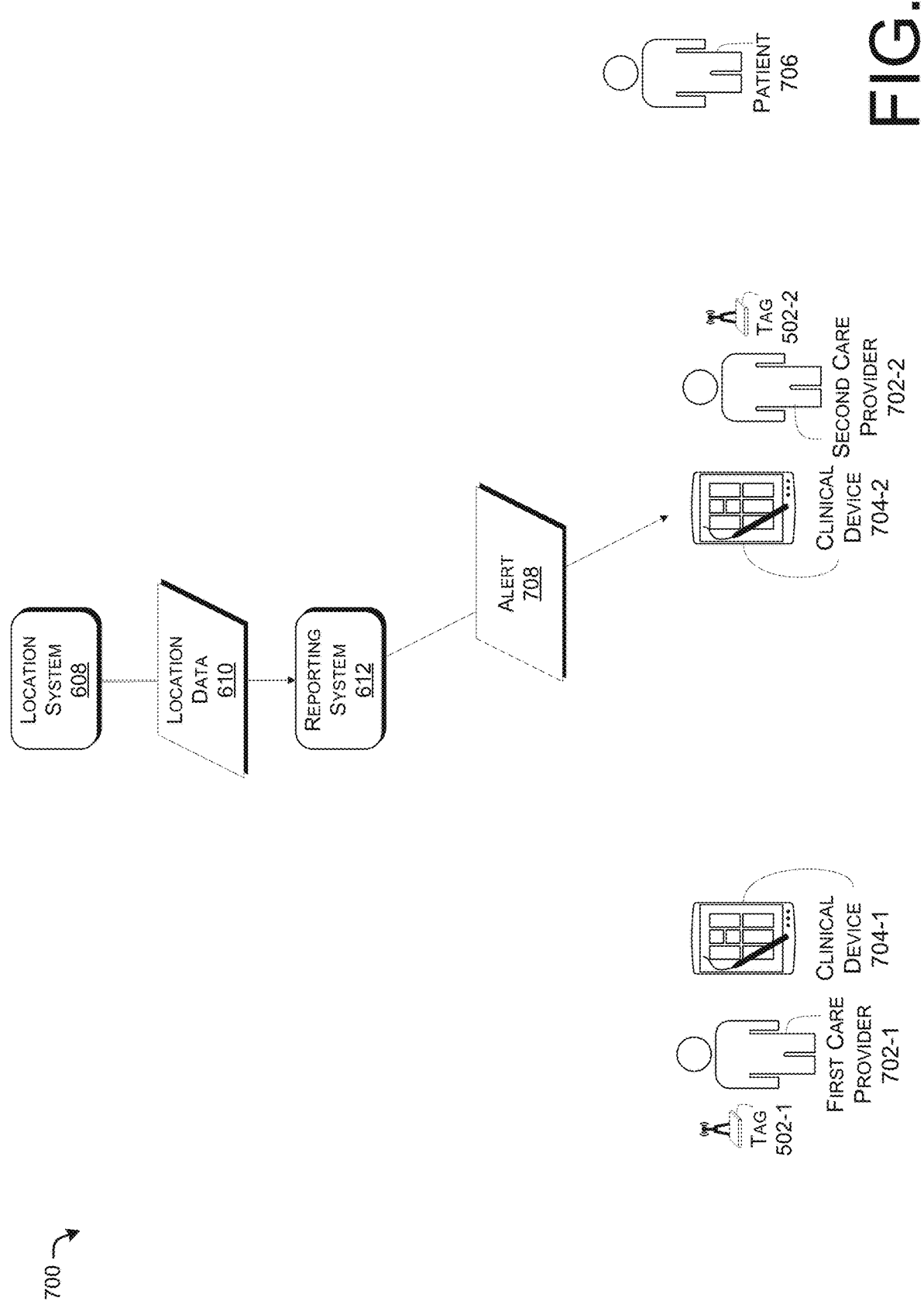
FIG. 7 illustrates an example environment of a location system being utilized in a clinical environment.

FIG. 7 illustrates an example environment 700 of a location system 608 being utilized in a clinical environment. As noted above, the location system 608 may provide the reporting system 612 with the location data 610. The location data 610 may indicate the locations of various tags (e.g., tag 502) throughout the clinical environment. In the example illustrated in FIG. 7, the location data 610 may indicate the locations of first and second tags 502-1 and 502-2 in the clinical environment.

First tag 502-1 may be worn by, held by, or attached to clinical provider 702-1. Clinical provider 702-1 may be associated with a clinical device 704-1. The clinical device 704-1 may be a mobile device, in some cases. In various implementations, the clinical device 704-1 could output alerts, instructions, or the like, to assist the clinical provider 702-1 with treating and monitoring patients within the clinical environment.

Similarly, second tag 502-2 may be worn by, held by, or attached to clinical provider 702-2. Clinical provider 702-2 may be associated with a clinical device 704-2. The clinical device 704-2 may be a mobile device, in some cases. In various implementations, the clinical device 704-2 could output alerts, instructions, or the like, to assist the clinical provider 702-2 with treating and monitoring patients within the clinical environment.

In various implementations, the reporting system 612 may identify that a patient 706 is in need of assistance from a clinical provider, such as either one of clinical providers 702-1 or 702-2. For example, the reporting system 612 may identify that the patient 706 is in need of non-emergency care (e.g., changing of a wound dressing, drug administration, or the like) or emergency care (e.g., defibrillation, tracheostomy, or the like). The reporting system 612 may also be aware of the location of the patient 706.

In some instances, at least one processor in the reporting system 612 may compare the location data 610 to the location of the patient to identify which one of the tags 502-1 or 502-2 is closest to the patient 706. For example, the reporting system 612 may determine that the second tag 502-2 is closer to the patient 706 than the first tag 502-1. Based on this comparison, the processor(s) in the reporting system 612 may identify that the tag 502-2 is closest to the patient 706.

The reporting system 612 may identify that the tag 502-2 is associated with the second care provider 702-2 and/or the clinical device 704-2 utilized by the second care provider 702-2. The reporting system 612 can selectively transmit an alert 708 to the clinical device 704-2. In response to receiving the alert, the clinical device 704-2 may output an instruction to provide assistance to the patient 706.

Figure 8:
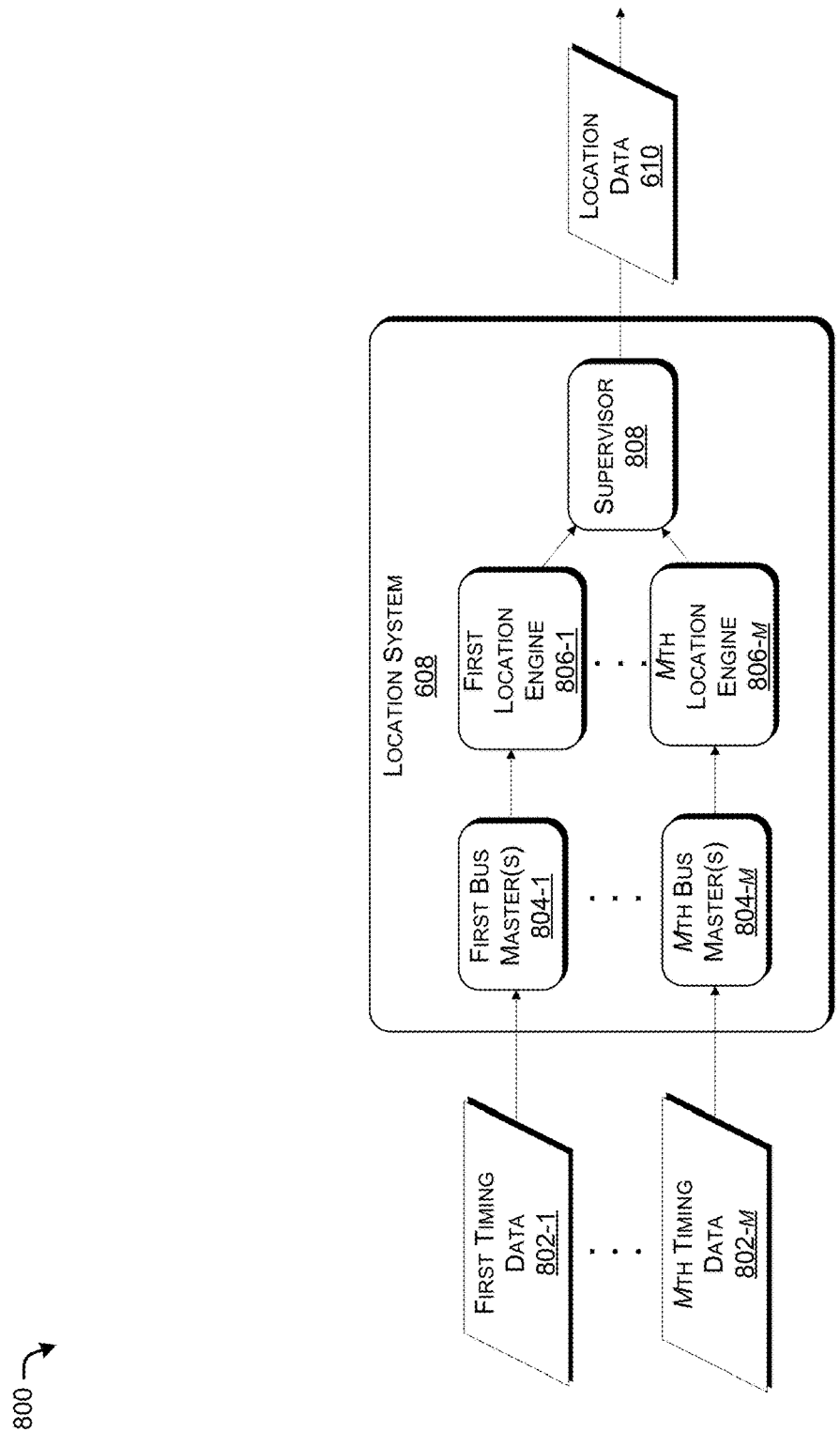
FIG. 8 illustrates an example environment for determining the locations of multiple tags in a clinical environment.

FIG. 8 illustrates an example environment 800 for determining the locations of multiple tags in a clinical environment. As illustrated, the environment 800 includes the location system 608 and the location data 610 described above with reference to FIG. 6.

First through mth timing data 802-1 to 802-$m$ may be received at first to mth bus masters 804-1 to 804-$m$ in the location system 608. The timing data 802-1 to 802-$m$ may represent timing data from multiple receivers receiving signals from multiple tags in the clinical environment. For instance, first timing data 802-1 may represent timing data from multiple primary receivers based on blinks from multiple tags. In some cases, the timing data 802-1 to 802-$m$ can be represented in data streams transferred from the primary receivers to the first to mth bus masters 804-1 to 804-$m$.

The bus masters 804-1 to 804-$m$ may each include hardware and/or software including a serial connection to which multiple receivers (e.g., multiple primary receivers) are connected. In various implementations, the bus masters 804-1 to 804-$m$ may be configured to orchestrate communications between the multiple receivers and other network nodes within the location system 606. In some cases, the bus masters 804-1 to 804-$m$ are connected to other network nodes within the location system 606 via a LAN.

In some cases, the bus masters 804-1 to 804-$m$ may generate individual data packets associated with single blink events (e.g., the same blink from the same tag) and transmit the individual data packets to the location engines 806-1 to 806-$m$. When the bus masters 804-1 to 804-$m$ receive timing data 802-1 to 802-$m$ from multiple primary receivers based on the same blink event, the bus masters 804-1 to 804-$m$ may be able to aggregate the subset of the timing data 802-1 to 802-$m$ from the same blink event into individual data packets.

The locating engines 806-1 to 806-$p$ may be configured to calculate the locations of the tags based on the data received from the bus masters 804-1 to 804-$m$. In some cases, $p<m$, such that there is a greater number of bus masters 804-1 to 804-$m$ than locating engines 806-1 to 806-$p$. For instance, multiple bus masters 804-1 to 804-$m$ may be connected to a single one of the locating engines 806-1 to 806-$p$.

A single supervisor (also referred to as an "aggregator") 808 may receive indications of the calculated locations from the location engines 806-1 to 806-$p$. The single supervisor 808 may aggregate the locations into location data 610. The location data 610 may be in the form of a data stream indicating individual tags and their calculated locations. Each one of the bus masters 804-1 to 804-$m$, locating engines 806-1 to 806-$p$, and the supervisor 808 may be a network node, in some cases.

Figure 9:
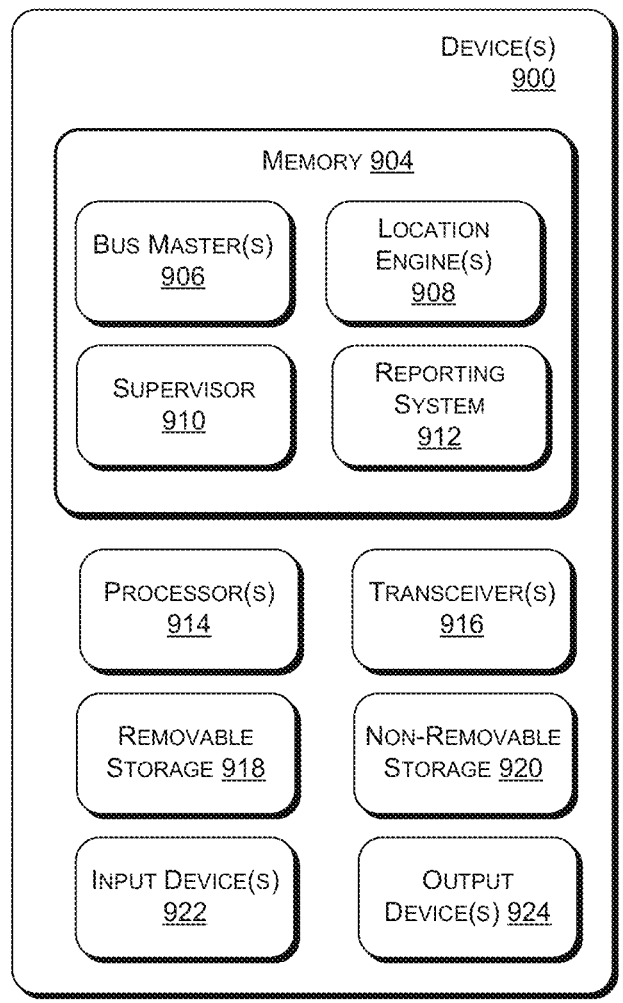
FIG. 9 illustrates at least one example device configured to enable and/or perform the some or all of the functionality discussed herein.

FIG. 9 illustrates at least one example device 900 configured to enable and/or perform the some or all of the functionality discussed herein. Further, the device(s) 900 can be implemented as one or more server computers 902, a network element on a dedicated hardware, as a software instance running on a dedicated hardware, or as a virtualized function instantiated on an appropriate platform, such as a cloud infrastructure, and the like. It is to be understood in the context of this disclosure that the device(s) 900 can be implemented as a single device or as a plurality of devices with components and data distributed among them.

As illustrated, the device(s) 900 comprise a memory 904. In various embodiments, the memory 904 is volatile (including a component such as Random Access Memory (RAM)), non-volatile (including a component such as Read Only Memory (ROM), flash memory, etc.) or some combination of the two.

The memory 904 may include various components, such as at least one bus master 906, at least one location engine 908, a supervisor 910, a reporting system 912, and the like. Any of the bus master(s) 906, the location engine(s) 908, the supervisor 910, and the reporting system 912 can comprise methods, threads, processes, applications, or any other sort of executable instructions. The bus master(s) 906, the location engine(s) 908, the supervisor 910, and the reporting system 912 and various other elements stored in the memory 904 can also include files and databases.

The memory 904 may include various instructions (e.g., instructions in the bus master(s) 906, location engine(s) 908, supervisor 910, and/or reporting system 912), which can be executed by at least one processor 914 to perform operations. In some embodiments, the processor(s) 914 includes a Central Processing Unit (CPU), a Graphics Processing Unit (GPU), or both CPU and GPU, or other processing unit or component known in the art.

The device(s) 900 can also include additional data storage devices (removable and/or non-removable) such as, for example, magnetic disks, optical disks, or tape. Such additional storage is illustrated in FIG. 9 by removable storage 918 and non-removable storage 920. Tangible computer-readable media can include volatile and nonvolatile, removable and non-removable media implemented in any method or technology for storage of information, such as computer readable instructions, data structures, program modules, or other data. The memory 904, removable storage 918, and non-removable storage 920 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 900. Any such tangible computer-readable media can be part of the device(s) 900.

The device(s) 900 also can include input device(s) 922, such as a keypad, a cursor control, a touch-sensitive display, voice input device, etc., and output device(s) D24 such as a display, speakers, printers, etc. These devices are well known in the art and need not be discussed at length here. In particular implementations, a user can provide input to the device(s) 500 via a user interface associated with the input device(s) 922 and/or the output device(s) D24.

As illustrated in FIG. 9, the device(s) 900 can also include one or more wired or wireless transceiver(s) 916. For example, the transceiver(s) 916 can include a Network Interface Card (NIC), a network adapter, a Local Area Network (LAN) adapter, or a physical, virtual, or logical address to connect to the various base stations or networks contemplated herein, for example, or the various user devices and servers. To increase throughput when exchanging wireless data, the transceiver(s) 916 can utilize Multiple-Input/Multiple-Output (MIMO) technology. The transceiver(s) 916 can include any sort of wireless transceivers capable of engaging in wireless, Radio Frequency (RF) communication. The transceiver(s) 916 can also include other wireless modems, such as a modem for engaging in Wi-Fi, WiMAX, Bluetooth, or infrared communication.

In some implementations, the transceiver(s) 916 can be used to communicate between various functions, components, modules, or the like, that are comprised in the device(s) 900. For instance, the transceivers 916 may facilitate communications between the bus master(s) 906, the location engine(s) 908, the supervisor 910, and/or the reporting system 912.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

Although the subject matter has been described in language specific to structural features and/or methodological acts, it is to be understood that the subject matter defined in the appended claims is not necessarily limited to the specific features or acts described.

The invention claimed is:

1. A location system, comprising:
at least one processor; and
memory storing instructions that, when executed by the at least one processor, cause the at least one processor to perform operations comprising:
receiving, from a primary receiver, timing data indicating times at which multiple receivers including the primary receiver received a wireless signal from a tag, the multiple receivers being located in a clinical environment;
consolidating the times at which the multiple receivers received the wireless signal into a single data packet;
determining a location of the tag based on the single data packet;
determining that the timing data includes a flag indicating that a user of the tag has requested assistance;
identifying an identifier of the tag based on the timing data; and
transmitting, to a reporting system, at least one first message indicating the location of the tag, an identifier of the tag, and that the user of the tag has requested assistance.

2. The location system of claim 1, wherein the operations further comprise:
identifying locations of the multiple receivers in the clinical environment, and
wherein determining the location of the tag comprises estimating the location of the tag based on the times in the single data packet and the locations of the multiple receivers.

3. The location system of claim 1, wherein the operations further comprise:
storing the timing data in at least one database; and
storing contents of the single data packet in the at least one database.

4. The location system of claim 1, wherein transmitting the first message to the reporting system comprises causing the reporting system to transmit, to an electronic device in the clinical environment, a request to assist the user of the tag.

5. The location system of claim 1, wherein the flag comprises a predetermined code in the timing data.

6. The location system of claim 1, wherein the flag indicates that a user of the tag has requested immediate assistance.

7. A system, comprising:
at least one processor; and
memory storing instructions that, when executed by the at least one processor, cause the at least one processor to perform operations comprising:
receiving, from a primary receiver, timing data indicating times at which multiple receivers including the primary receiver received a wireless signal from a tag, the multiple receivers being located in a clinical environment;
consolidating the times at which the multiple receivers received the wireless signal into a single data packet;
determining a location of the tag based on the single data packet;
determining that the timing data includes a flag indicating that a user of the tag has requested assistance;
identifying an identifier of the tag based on the timing data;
identifying the user of the tag based on the identifier; and
transmitting, to the electronic device, at least one message indicating the location of the tag, the user, and that the user has requested assistance.

8. The system of claim 7, wherein transmitting the at least one message comprises causing the electronic device to output an instruction to assist a user of the tag.

9. The system of claim 7, wherein the operations further comprise:
identifying locations of the multiple receivers in the clinical environment, and wherein determining the location of the tag comprises estimating the location of the tag based on the times in the single data packet and the locations of the multiple receivers.

10. The system of claim 7, wherein transmitting the at least one message comprises causing the electronic device to output the location of the tag.

11. The system of claim 7, wherein the operations further comprise:
storing the timing data in at least one database; and
storing the single data packet in the at least one database.

12. The system of claim 7, wherein the flag comprises a predetermined code in the timing data.

13. The system of claim 7, wherein the flag indicates that a user of the tag has requested immediate assistance.

14. A system, comprising:
a tag;
multiple receivers located in a clinical environment;
at least one processor; and
memory storing instructions that, when executed by the at least one processor, cause the at least one processor to perform operations comprising:
receiving, at the tag, a trigger indicating that a user of the tag has requested assistance;
generating, by the tag, a wireless signal including a flag indicating that the tag is triggered;
transmitting, by the tag, the wireless signal to the multiple receivers in a clinical environment;
transmitting, by the multiple receivers, timing data including the flag to a location system;
identifying, by the location system, that the timing data includes the flag;
identifying, by the location system, times at which the multiple receivers received the wireless signal from the tag;
consolidating, by the location system, the times at which the multiple receivers received the wireless signal into a single data packet;
determining, by the location system, a location of the tag based on the single data packet;
identifying an identifier of the tag based on the timing data; and
transmitting, by the location system to a reporting system, at least one message indicating the location of the tag, an identifier of the tag, and that the user of the tag has requested assistance.

15. The system of claim 14, wherein receiving the trigger comprises receiving an indication that a button of the tag has been pressed.

16. The system of claim 14, wherein the at least one message further indicates an identifier of the user.

17. The system of claim 14, wherein transmitting the wireless signal to the multiple receivers in the clinical environment comprises:
transmitting, by the tag to a primary receiver, the wireless signal; and
transmitting, by the tag to a secondary receiver, the wireless signal,
wherein transmitting the timing data to the location system comprises:
transmitting, by the secondary receiver to the primary receiver, a report indicating a first time at which the secondary receiver received the wireless signal; and
transmitting, by the primary receiver to the location system, the timing data comprising the first time and a second time at which the primary receiver received the wireless signal.

18. The system of claim 14, wherein the operations further comprise:
identifying, by the location system, locations of the multiple receivers in the clinical environment, and
wherein determining the location of the tag comprises estimating, by the location system, the location of the tag based on the times in the single data packet and the locations of the multiple receivers.

19. The system of claim 18, wherein the operations further comprise:
storing, by the location system, the timing data in at least one database; and
storing, by the location system, the single data packet in the at least one database.

20. The system of claim 14, wherein transmitting the at least one message to the reporting system comprises causing the reporting system to transmit, to an electronic device in the clinical environment, a request to assist the user of the tag.

* * * * *